US012695248B2

(12) United States Patent (10) Patent No.: US 12,695,248 B2
Haslinger et al. (45) Date of Patent: Jul. 28, 2026

(54) INTERFACE ASSEMBLY

(71) Applicant: Otto Bock Healthcare Products GmbH, Vienna (AT)

(72) Inventors: Martin Haslinger, Vienna (AT); Dusan Vujanic, Vienna (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 682 days.

(21) Appl. No.: 18/011,974

(22) PCT Filed: Jun. 23, 2021

(86) PCT No.: PCT/EP2021/067118
§ 371 (c)(1),
(2) Date: Dec. 21, 2022

(87) PCT Pub. No.: WO2021/259985
PCT Pub. Date: Dec. 30, 2021

(65) Prior Publication Data
US 2023/0253734 A1     Aug. 10, 2023

(30) Foreign Application Priority Data

Jun. 23, 2020     (DE) ...................... 10 2020 116 481.5

(51) Int. Cl.
*H01R 13/639* (2006.01)
*A61F 2/70* (2006.01)
(Continued)

(52) U.S. Cl.
CPC ............. *H01R 13/639* (2013.01); *A61F 2/70* (2013.01); *H01R 13/5219* (2013.01); *A61F 2002/5083* (2013.01); *H01R 13/24* (2013.01)

(58) Field of Classification Search
CPC ........................... H01R 13/639; H01R 13/5219
(Continued)

(56) References Cited

U.S. PATENT DOCUMENTS 3,141,721 A     7/1964 Horn
4,113,217 A *   9/1978 O'Connell .............. B60R 11/02
292/87
(Continued)

FOREIGN PATENT DOCUMENTS

DE     19654275 A1     7/1997
DE     10252900 B4     6/2004
(Continued)

OTHER PUBLICATIONS

International Search Report and Written Opinion for International Patent Application No. PCT/EP2021/067118, mailed Nov. 4, 2021.

*Primary Examiner* — Neil Abrams
(74) *Attorney, Agent, or Firm* — Goodwin Procter LLP

(57) ABSTRACT

The invention relates to an interface assembly comprising a first interface component (10) and a second interface component (20) with a sliding guide (30) for mechanically securing the interface components (10, 20) to one another, wherein a tongue (12) projecting from a base (11) is situated on one of the interface components (10) and a groove (22) located in a base (21) is situated on the other interface component (20), the tongue and groove having corresponding cross-sections, wherein the tongue (12) and the groove (22) interlockingly secure the interface components (10, 20) to one another and block a movement perpendicular to the bases and perpendicular to the longitudinal extent of the tongue (12) and groove (22), wherein electrical contact elements (15, 25) are situated on the tongue (12) and in the groove (22) and establish an electrical connection when the interface components (10, 20) are joined.

14 Claims, 11 Drawing Sheets

Figure 1:
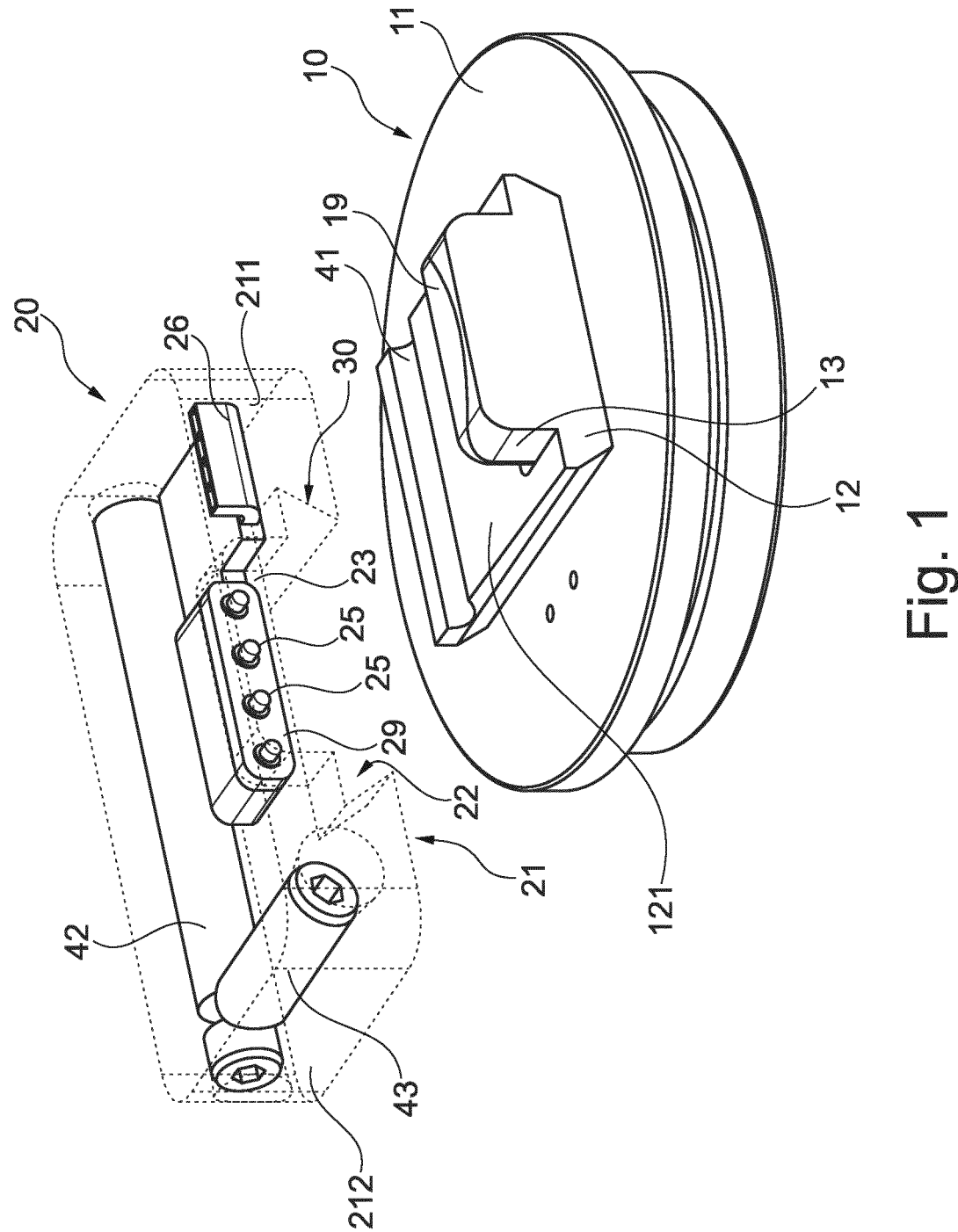

(51) Int. Cl.
    *H01R 13/52*       (2006.01)
    *A61F 2/50*        (2006.01)
    *H01R 13/24*       (2006.01)

(58) Field of Classification Search
    USPC ......................................................... 439/929
    See application file for complete search history.

(56)             References Cited

U.S. PATENT DOCUMENTS

| | | | | |
|---|---|---|---|---|
| 5,431,570 | A * | 7/1995 | Gibbs | B62D 35/007 |
| | | | | 29/854 |
| 5,744,934 | A * | 4/1998 | Wu | H01R 27/00 |
| | | | | 320/111 |
| 5,975,935 | A | 11/1999 | Yamaguchi et al. | |
| 6,190,194 | B1 * | 2/2001 | Kubota | H01R 13/631 |
| | | | | 439/378 |
| 6,729,413 | B2 * | 5/2004 | Turner | H01M 50/247 |
| | | | | 173/217 |
| 6,783,403 | B2 * | 8/2004 | Lafragette | H01R 4/484 |
| | | | | 439/717 |
| 7,070,458 | B2 * | 7/2006 | Axenbock | H01R 13/2421 |
| | | | | 439/700 |
| 7,271,760 | B2 * | 9/2007 | Bartosik | G01S 7/022 |
| | | | | 342/175 |
| 8,425,620 | B2 | 4/2013 | Johnson et al. | |
| 2014/0295689 | A1 * | 10/2014 | Zhao | H01R 13/516 |
| | | | | 439/271 |
| 2015/0064955 | A1 | 3/2015 | Liu | |
| 2020/0315817 | A1 | 10/2020 | Kaitan et al. | |

FOREIGN PATENT DOCUMENTS

| | | |
|---|---|---|
| DE | 102007026151 A1 | 11/2007 |
| DE | 102012013948 A1 | 1/2014 |
| DE | 102017131193 A1 | 6/2019 |
| DE | 102018107176 A1 | 9/2019 |
| EP | 2219272 B1 | 3/2014 |
| WO | 2014009368 A1 | 1/2014 |

* cited by examiner

INTERFACE ASSEMBLY

CROSS-REFERENCE TO RELATED APPLICATIONS

This application is a U.S. national phase filing claiming the benefit of and priority to International Patent Application No. PCT/EP2021/067118, filed Jun. 23, 2021, which claims priority from and the benefit of German Patent Application No. 10 2020 116 481.5, filed Jun. 23, 2020. The entire contents of these applications are incorporated herein by reference.

The invention relates to an interface assembly with a first interface component and a second interface component with a sliding guide for mechanically fixing the interface components to one another, wherein a tongue projecting from a base surface is arranged on one of the interface components and a groove located in a base surface with corresponding cross sections is arranged on the other interface component, wherein the tongue and the groove fix the interface components to one another in a form-fitting manner and block a movement perpendicular to the base surfaces and perpendicular to the longitudinal extension of the tongue and groove. In particular, such an interface assembly is provided on orthopedic devices, wherein the interface components may be parts of components of an orthopedic system. The interface components may be arranged or formed on one of the respective components and allow the two components to be mechanically fixed to each other. In particular, the interface components are part of prosthetic components, for example prosthetic hands, prosthetic feet, prosthetic knees. However, the application and use of the interface components to form the interface assembly is not limited to prostheses; orthoses or exoskeletons or other orthopedic devices may also have or form such an interface arrangement.

Orthopedic systems consist of several components that must be arranged and fixed to each other. In the process, interfaces arise at the transitions of the respective components, since the respective orthopedic device or other systems cannot or should not be designed in one piece. Interfaces must be provided in particular for interchangeable arrangement. Orthoses have, for example, joints that articulate an upper part to a lower part. So-called rail boxes are formed on such an orthotic joint, which serve to accommodate the respective rail. The rail boxes are manufactured as a groove that surrounds a rail on four sides. Fixation is usually by means of screws.

In prosthesis systems, the prosthetic components are often fixed to one another by means of a so-called pyramid adapter, in which one component has a base surface curved outwards in the shape of a dome, from which a four-sided pyramid protrudes with the tip pointing downwards. The corresponding other prosthetic component has an inwardly curved dome surface with a recess for the truncated pyramid. Laterally, fixing screws are moved in the direction of the lateral surfaces of the pyramid in order to achieve adjustment of the components relative to one another and their form-fit fixing to one another.

In principle, it is also known to fix prosthetic components or other orthopedic components to one another by means of a so-called sliding guide. For this purpose, a tongue is arranged in one component, opposite which is a correspondingly shaped groove on the other component. To connect the two components, the groove is inserted into the tongue so that the two components are fixed to each other. Blocking of the movement against the direction of insertion is achieved, for example, by screws to prevent the tongue from being unintentionally moved out of the groove.

In more and more orthopedic systems electrical and electronic components are used, which leads to problems with the transmission of electrical signals to the individual components. The transmission of data as well as the transport of sufficient amounts of electrical energy often requires a cable-based connection of individual components, so that, especially in the area of the mechanical interface, an electrical interface is also added. This is often implemented via plugs or sliding contacts. Such an electrical interface is susceptible to contamination and carries the risk that the plug components may become detached from one another.

It is the task of the present invention to provide an interface assembly which does not have the disadvantages described above. According to the invention, this task is solved by an interface assembly having the features of the main claim. Advantageous embodiments and further embodiments of the invention are disclosed in the subclaims, the description and the figures.

The interface assembly with a first interface component and a second interface component with a sliding guide for mechanically fixing the interface components to one another, wherein a tongue projecting from a base surface is arranged on one of the interface components and a groove with corresponding cross sections located in a base surface is arranged on the other interface component, wherein the tongue and the groove fix the interface components to one another in a form-fitting manner and block movement perpendicular to the base surfaces and perpendicular to the longitudinal extension of the tongue and groove, provides that electrical contact elements are arranged on the tongue and in the groove which establish an electrical connection in a joined state of the interface component. The combination of a mechanical interface and a mechanical fixing of several interface components to each other with an electrical interface by means of contacts arranged on the groove and in the tongue results in a sealed, mechanically fixed, electrical interface with a very small installation space requirement. At the same time, it is ensured that when the two interface components are mechanically locked to each other, an electrical interface is also securely formed, eliminating the possibility of unintentional false contacts. Incorrect assembly is virtually ruled out and the assembly effort is kept to a minimum thanks to simple, fast and safe assembly and disassembly of the interface partners. It is no longer necessary to lay cables across an interface, and bending stresses and alternating loads at a cable connection are no longer present.

In a further embodiment of the invention, it is provided that the electrical contact elements for establishing the electrical connection are arranged in an end face of an end stop of the tongue and/or on an end face of the end stop of the groove. This ensures that when the first interface component is fully assembled and fully inserted into the second interface component, there is a fully automatic, positively coupled and sealed contact connection. If the two interface components are correctly mechanically interlocked, there is also a correct electrical connection.

The end stop can form a contact surface for a plug or socket with the contact elements. This provides additional mechanical interlocking and protection of the electrical components when the plug components are inserted into the socket components once the groove and the tongue are engaged.

In one further embodiment of the invention, the groove in the joined state is sealed with the tongue at the front face, for example by a seal on the tongue arranged at the rear and/or front end, by a projection or end stop, optionally with a seal or by arrangement of a corresponding seal in the groove wall. Furthermore, the sealed groove prevents or at least reduces the penetration of dirt and moisture into the mechanical connection and thereby also into the electrical contacting, so that a permanently reliable contacting can be provided.

Advantageously, a cable connection leads from the electrical contact elements away from the tongue and groove through the respective interface components, so that there is no relative movement in the area of the electrical contacting between the individual cables or cable feeds. This prevents complicated routing of cables outside the interface components and ensures that the cables are routed correctly.

In at least one of the interface components, a cable duct and/or a plug receiver may be arranged or formed to guide the cables accordingly within the interface component or to receive plugs so that electrical contacting can take place. The electrical contact elements are formed, for example, in a plug that can be formed separately and inserted and fixed in the plug receiver in the interface component.

The interface components can have a locking device that blocks displacement of the interface components relative to one another along the longitudinal extent of the sliding guide. The arrangement of the locking device on the interface components enables integration also of a mechanical fixing in the respective interface component. Separate components are then no longer required for mounting the individual interface components to one another, since the components of the locking device are arranged on the interface components.

The locking device may include two form-fitting components that can be repeatably engaged with and disengaged from each other. This allows the individual components to be repeatedly locked to and disengaged from each other. One of the two form-fitting components may be rotatably or pivotally mounted to or within an interface component and may include at least one flattened portion, a non-circular cross-section, or a recess. The rotatability or pivotability of the form-fitting component makes it possible, in addition to simply locking and blocking the mobility against the direction of insertion, to cause the sliding guide to be braced against one another. The individual lateral surfaces and contact surfaces of the sliding guide are braced against each other, so that a secure hold is provided by form-fitting locking and, in addition, play compensation is provided by axial or radial bracing of the joining surfaces of the sliding guide.

As a result, the individual components of the slide guide can be manufactured with less precision, the overall design is more error-tolerant, exhibits a low degree of complexity and enables favorable manufacturing of the entire interface assembly.

Advantageously, the form-fitting component braces the interface components against each other in the locked position, thus effecting a clamping connection between the individual interface components.

One of the form-fitting components can have a securing element assigned to it, which is accessible from one end face of the interface component. This makes it possible to assemble and lock the interface components in only one joining direction, so that simple and fast as well as secure locking of the interface components to one another is possible, even when installation space is limited and accessibility is poor, which is more often the case in orthopedic devices.

The securing element of the form-fitting component can engage in the form-fitting element in a form-fitting manner, for example by snapping into a recess or being inserted into a recess. Alternatively or additionally, the securing element can be preloaded against the form-fitting element or coupled to the form-fitting element via a toothing. The toothing is advantageously designed to be self-locking, so that displacement and thus release or locking of the form-fitting element in the locked or unlocked position is only possible by appropriate actuation of the securing element.

One of the form-fitting components can be formed as a groove, providing a large surface area with which the other form-fitting component can interact. This reduces the surface pressure, which means that the individual form-fitting components can be designed to be comparatively small. This increases the scope for design solutions and reduces the required installation space.

The first interface component can be formed as a distal end plate of a prosthetic socket or a prosthetic component, and the second interface component can be formed as a proximal end component of a prosthetic hand or a prosthetic gripping device.

Figure 2:
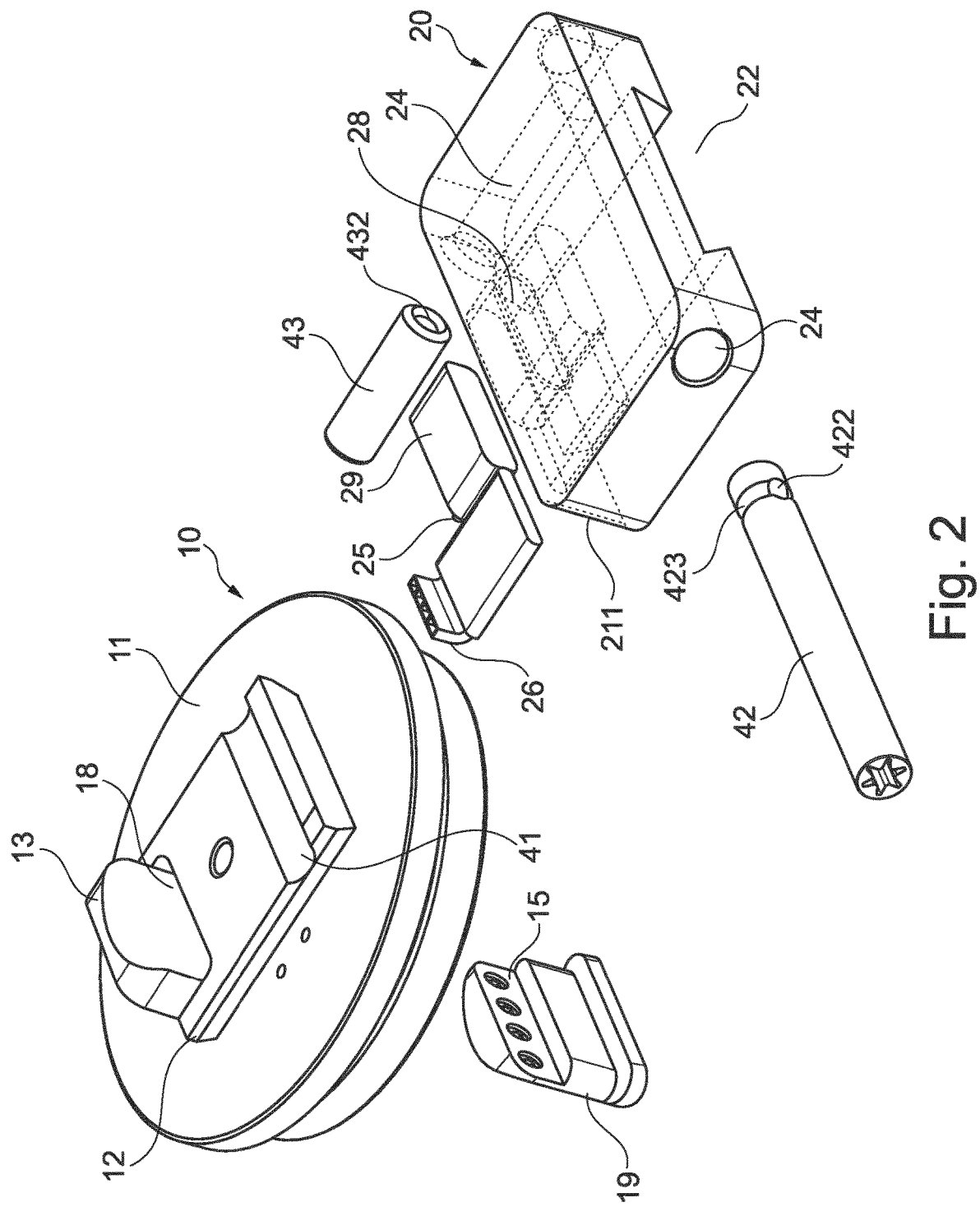
Figure 3:
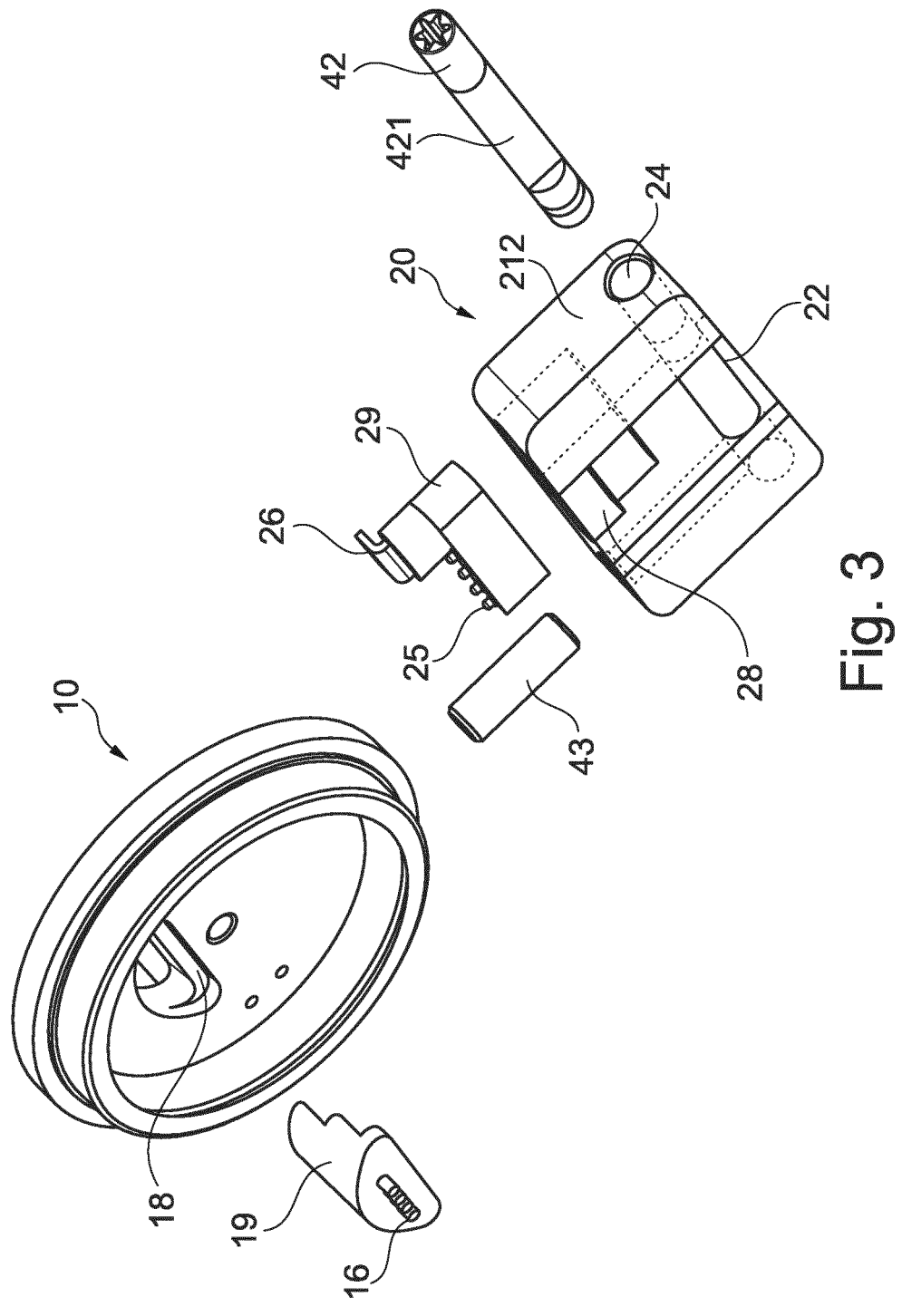
Figure 4:
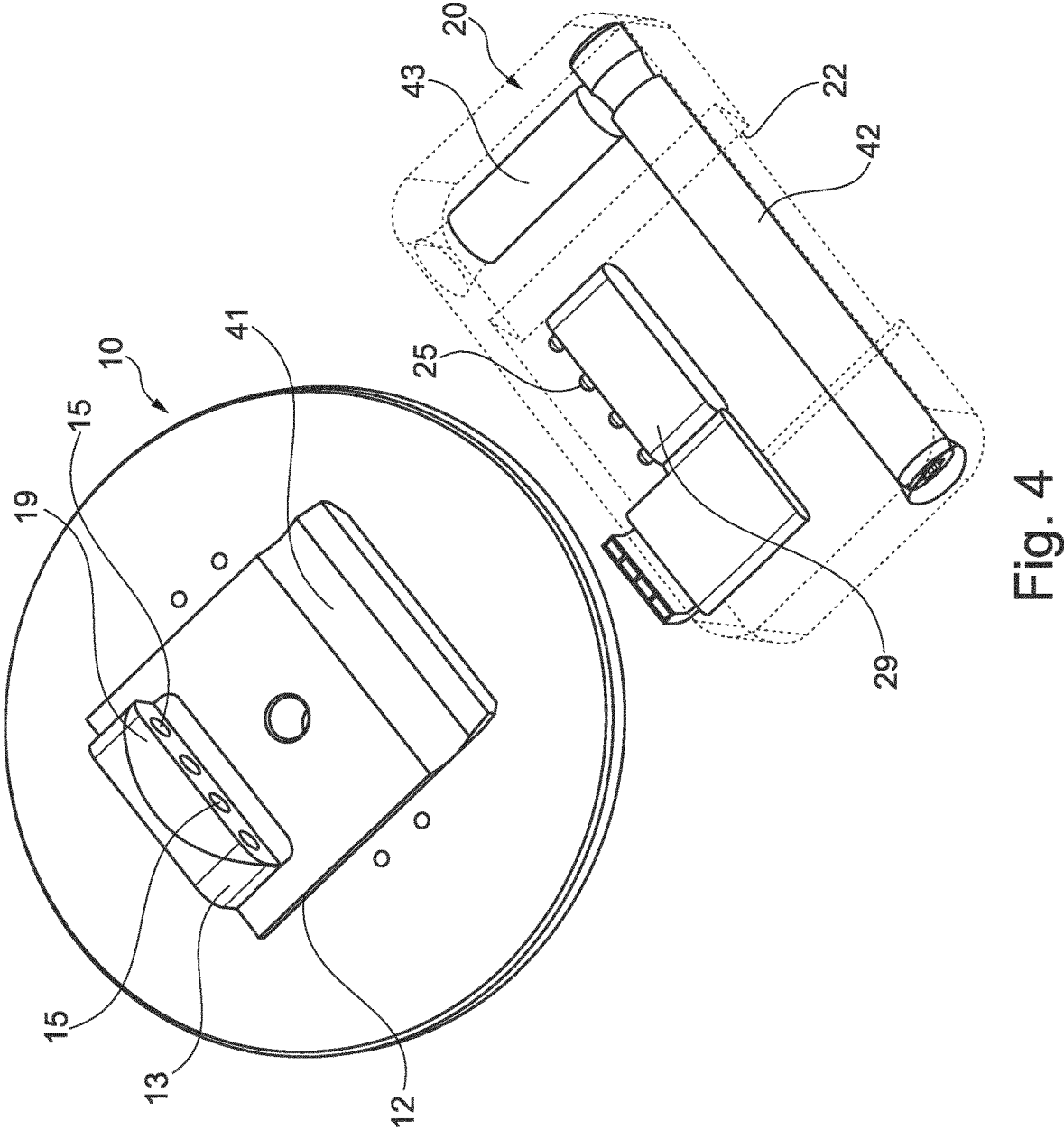
Figure 5:
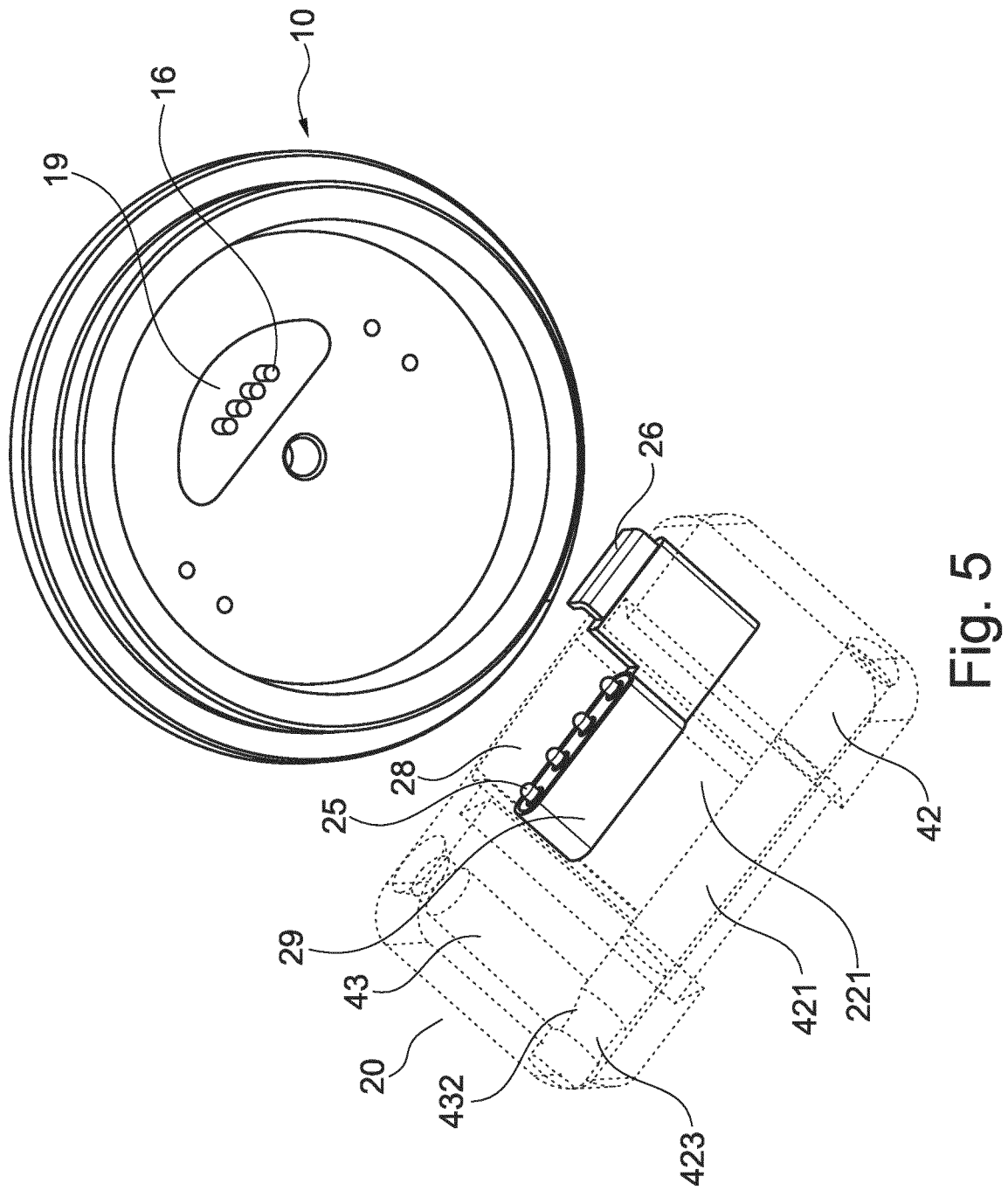
Figure 6:
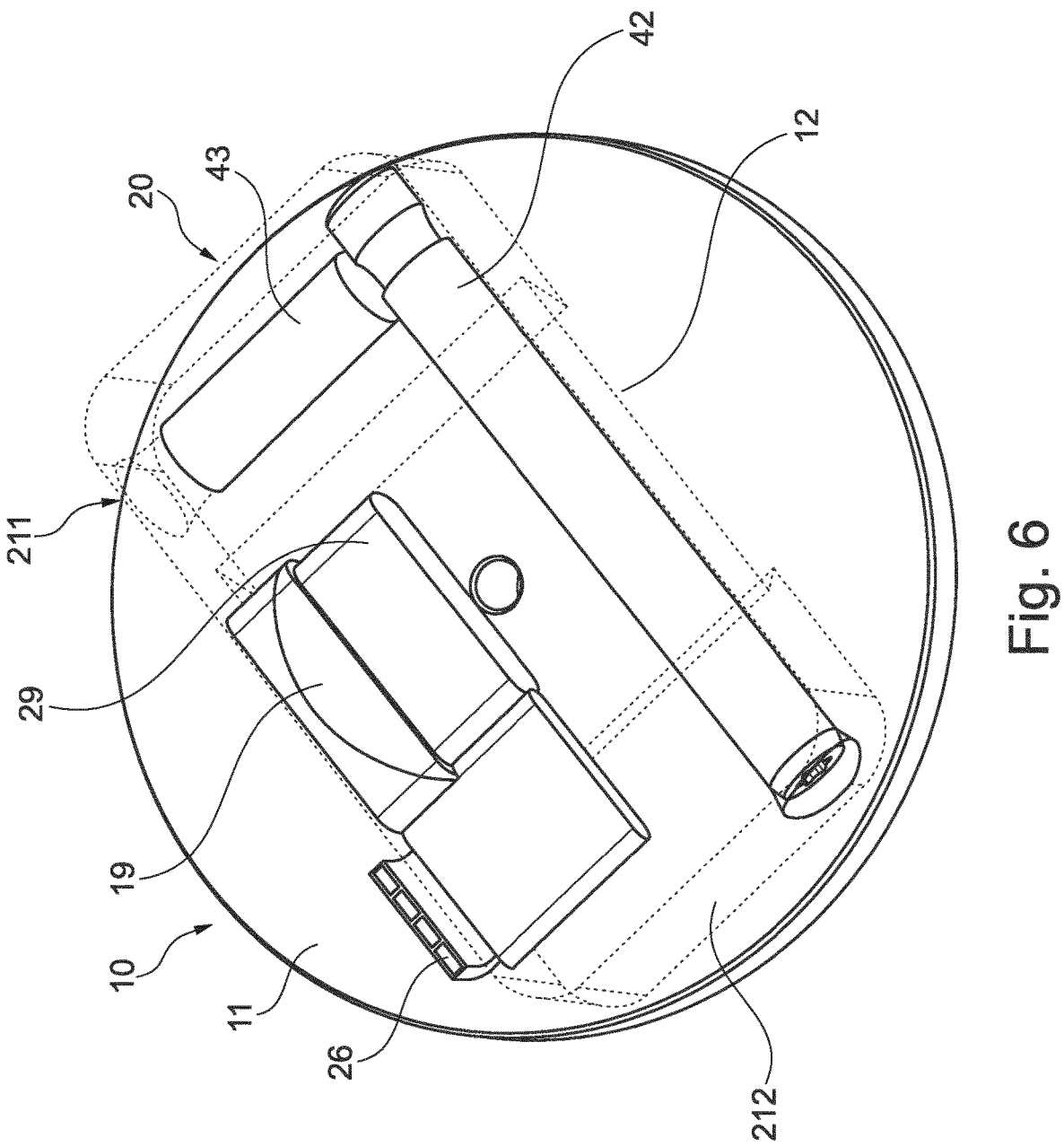
Figure 7:
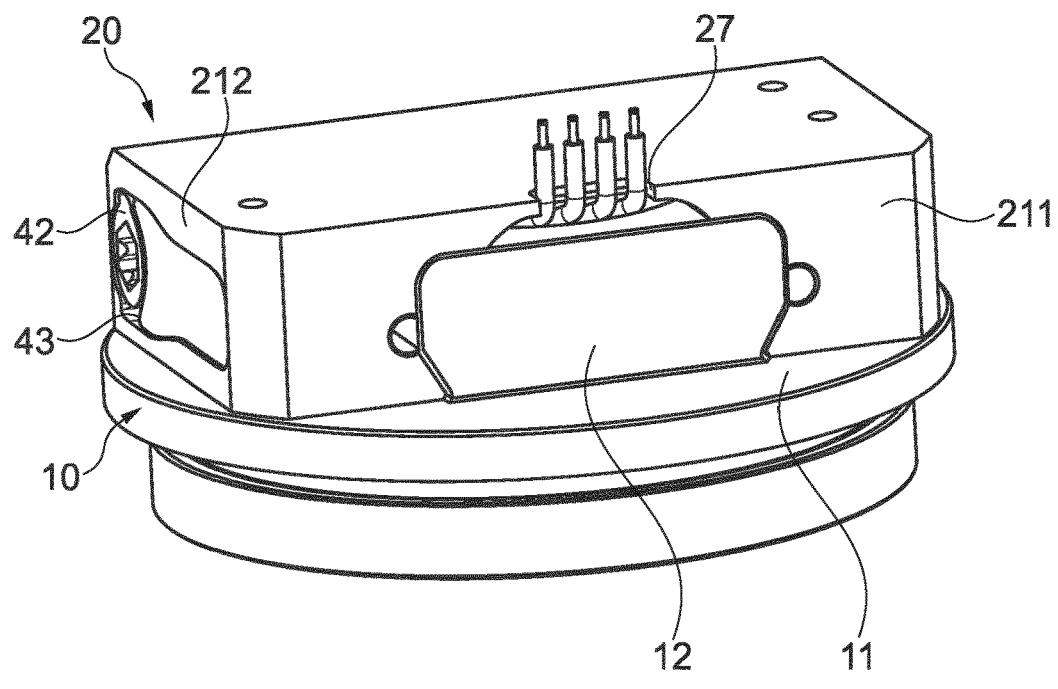
Figure 8:
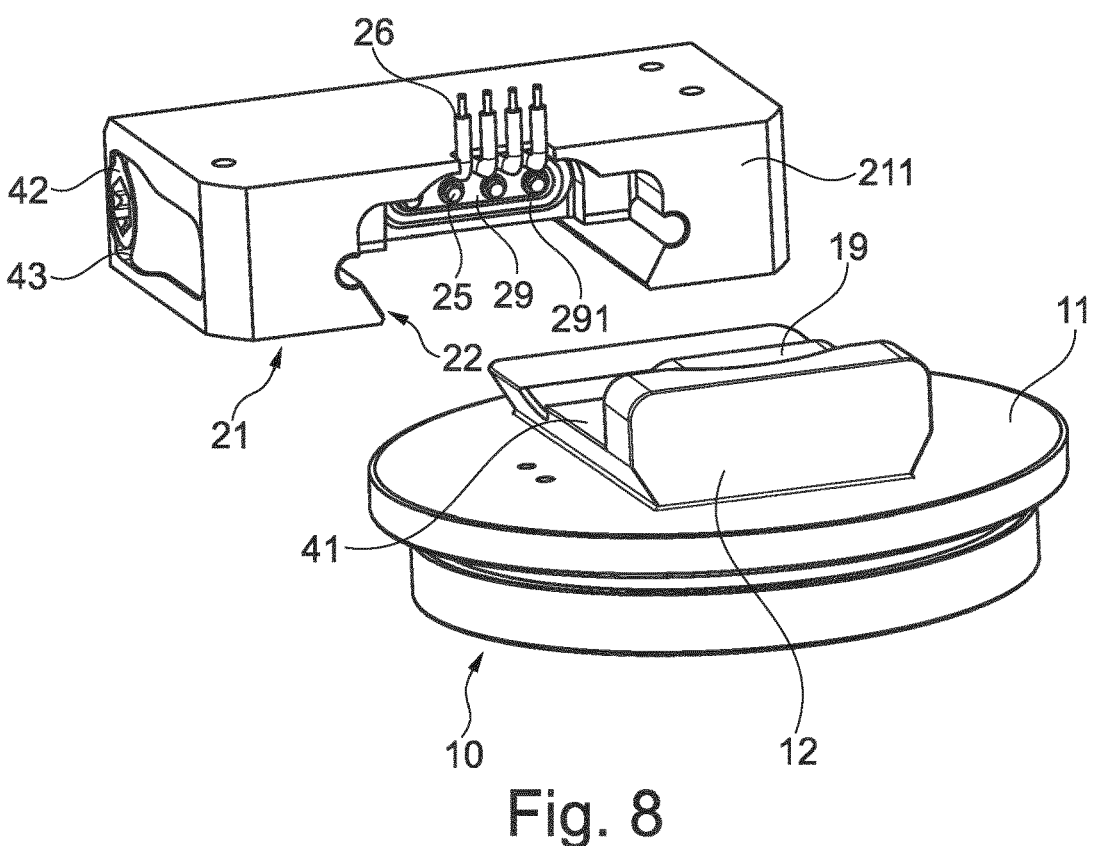
Figure 9:
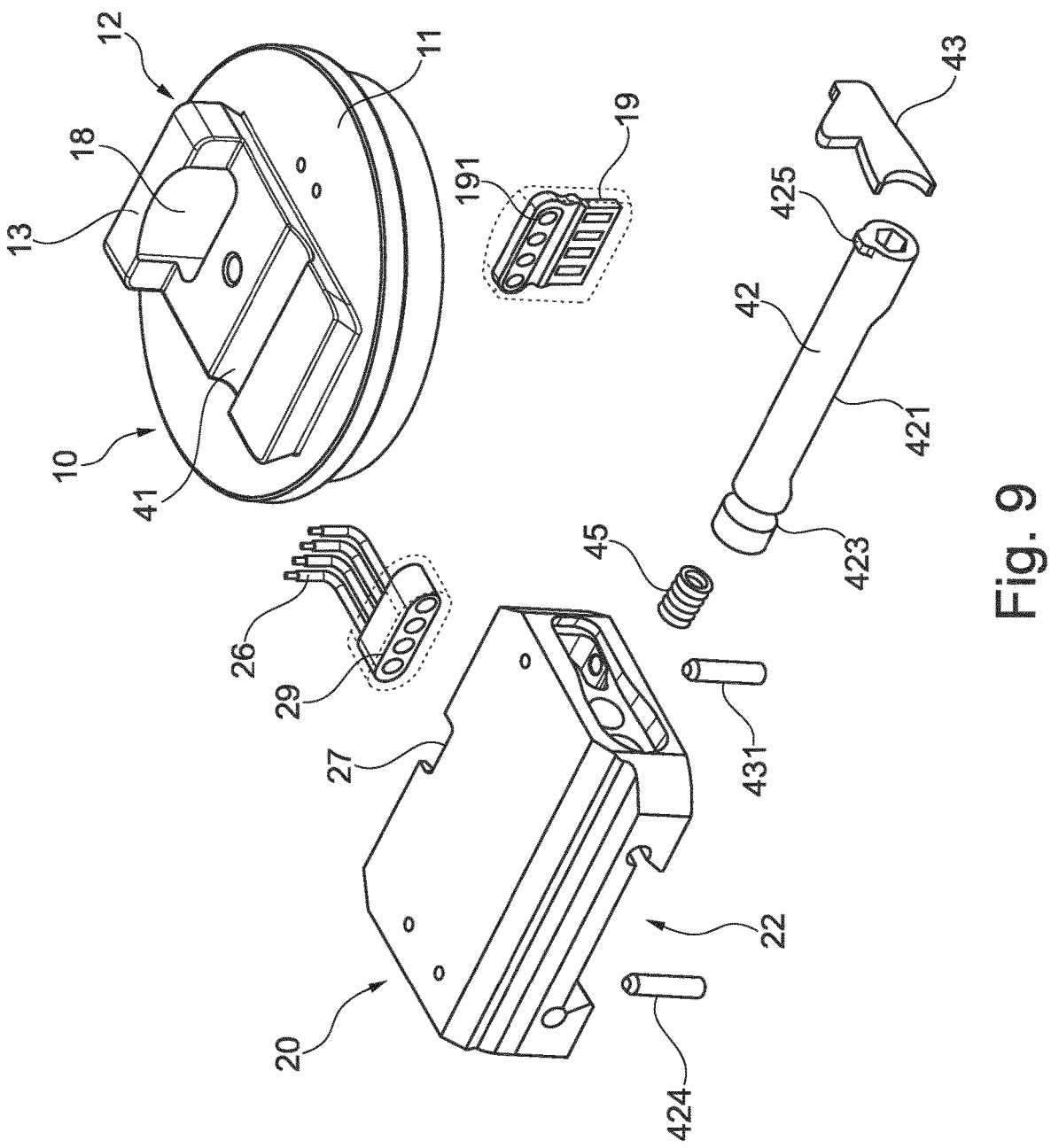
Figure 10:
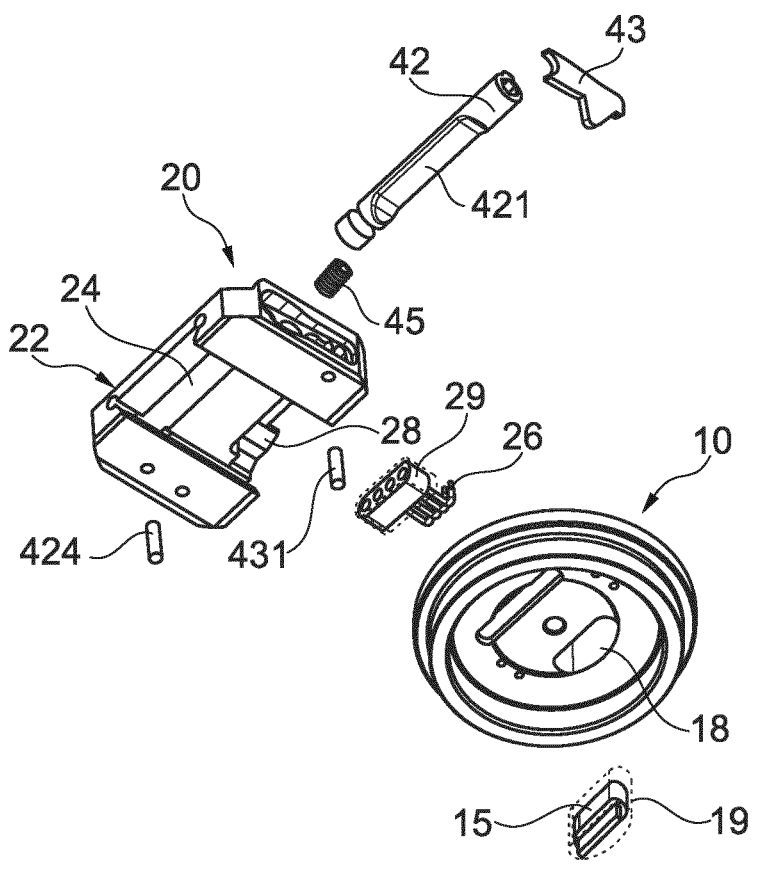
Figure 11:
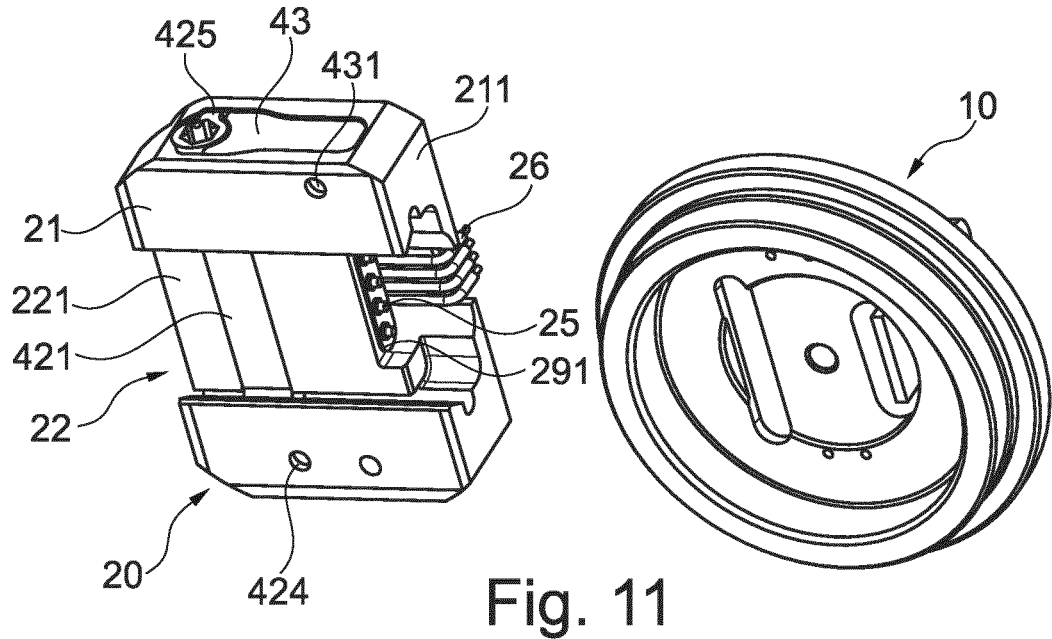
Figure 12:
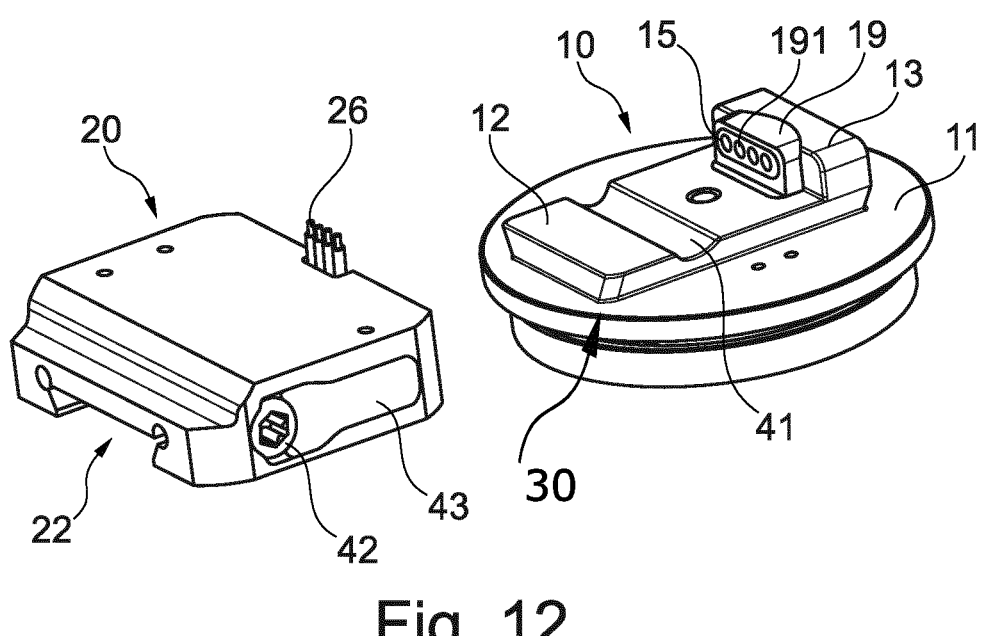
Figure 13:
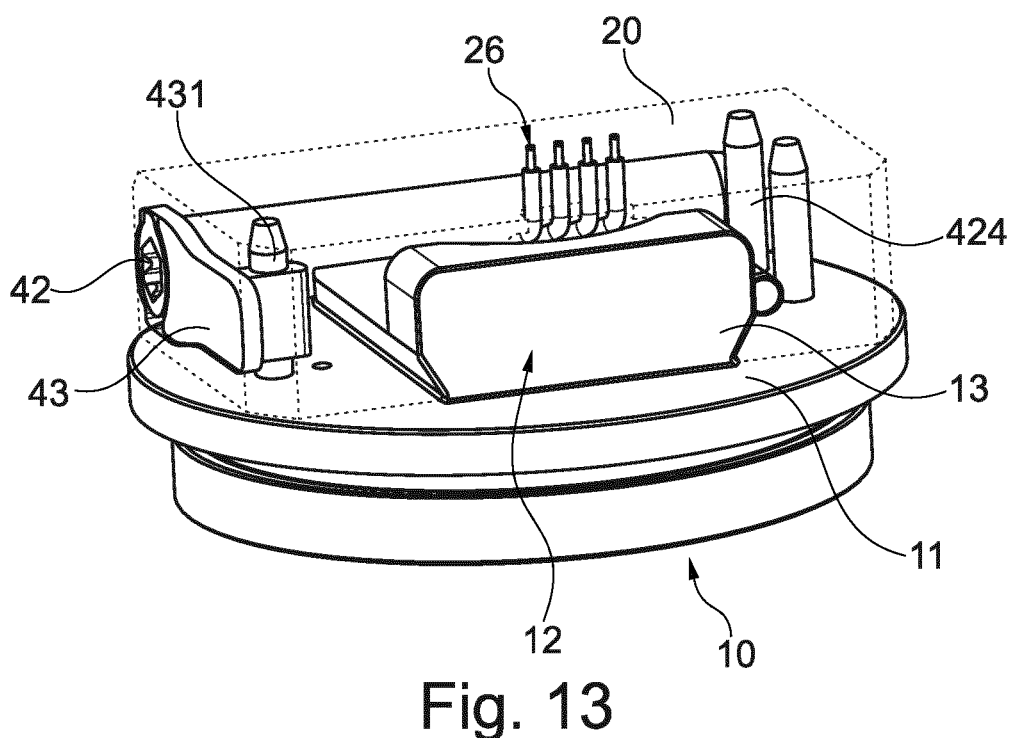
Figure 14:
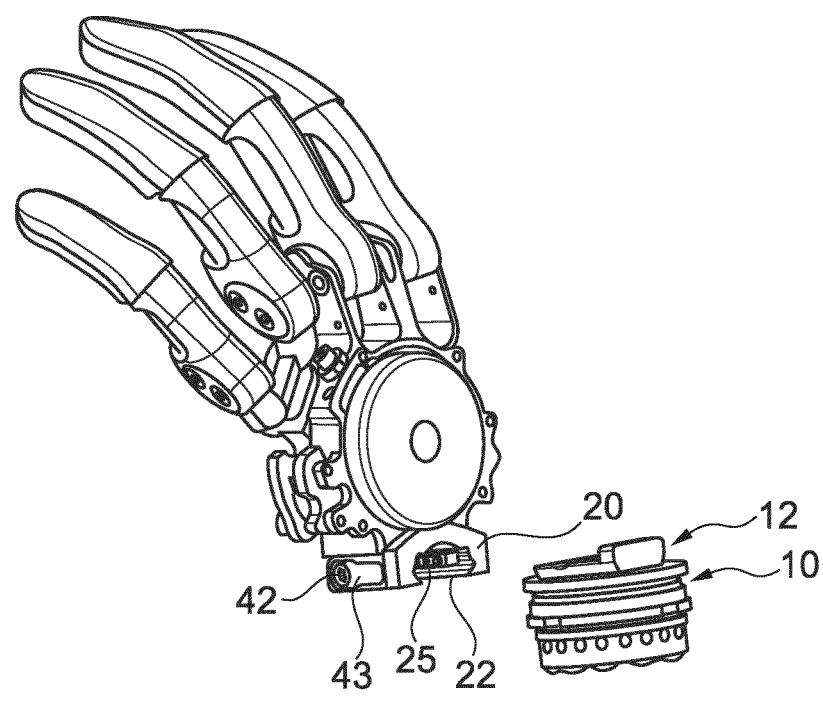

In the following, embodiments of the invention are explained in more detail with reference to the accompanying figures. They show:

FIG. 1—a perspective view of an interface assembly with two interface components in a non-joined state;

FIG. 2—an exploded view of the components of FIG. 1;

FIG. 3—a bottom view of the representation of FIG. 2;

FIG. 4—an oblique plan view of the interface assembly in the unjoined state as shown in FIG. 1;

FIG. 5—a bottom view of the position according to FIG. 4;

FIG. 6—an illustration of the interface assembly with joined interface components;

FIG. 7—an alternative embodiment in the joined state;

FIG. 8—FIG. 7 in non-joined state;

FIG. 9—an exploded view of the components of the embodiment according to FIG. 8;

FIG. 10—a bottom view of FIG. 9;

FIG. 11—a bottom view of the interface components;

FIG. 12—a different view of FIG. 8;

FIG. 13—a partially transparent view in the assembled state;

FIG. 14—an example of use of the invention on a prosthetic hand; and

Figure 15:
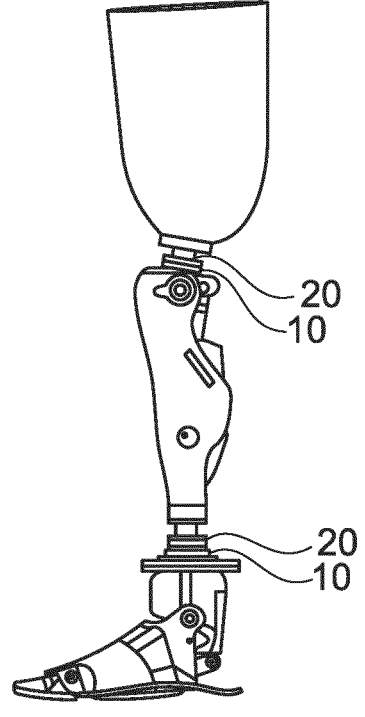

FIG. 15—an example of use of the invention on a prosthetic leg.

FIG. 1 shows a perspective view of an interface assembly comprising a first interface component 10 and a second interface component 20. The second interface component 20 is shown only in broken lines in the outline view to show the parts of the second interface component 20 that are not otherwise visible. The first interface component 10 has a base surface 11 from which a tongue 12 extends. If the first interface component 10 is formed as a proximal component, the tongue 12 extends distally from the base surface 11 when the interface assembly is a connection in the context of orthopedic technology. The tongue 12 is in the form of a modified dovetail tongue and includes an upwardly projecting end stop 13, which projects above a tongue surface 121, that is arranged essentially parallel to the base surface 11. A form-fitting component 41 in the form of a recess, groove or channel is formed Within the tongue surface 121, extending transversely to the longitudinal extension of the tongue 12. The form-fitting component 41 is arranged within the tongue surface 121, the tongue surface 121 thus extending from the form-fitting component 41 on both sides of the longitudinal extension of the tongue 12. A plug 19 is arranged within the tongue 12 and is located between the end stop 13 and the form-fitting component 41. The plug 19 abuts the end stop 13 and extends beyond the tongue surface 121, but not beyond the end stop 13.

The second interface assembly 20, which may be arranged or formed on a distal component of an orthopedic device, for example, includes a groove 22 that is shaped to correspond to the tongue 12. The groove 22 extends away from an end face 212 into the second interface component 20. A base surface 21 is formed on the underside from which the groove 22 extends upwardly. Advantageously, the base surface 21 of the second interface component 20 is designed to rest on or abut the base surface 11 of the first interface component 10, at least forming only a small gap therebetween. A plug 29 with electrical contacts 25 is arranged within the groove 22 at an end thereof that faces away from the end face 211. The plug 29 is essentially flush with an end stop 23, and the electrical contacts 25 or plug elements advantageously project beyond the end stop 23.

Further, holes are arranged in the second interface component 20 extending perpendicularly from the end face 211 along the longitudinal extension of the groove 22 as well as perpendicularly thereto. A second form-fitting component 42 is arranged in the bore extending transversely to the longitudinal extent of the groove 22, which can provide a form-fitting locking with the first form-fitting component 41 in the tongue 12. The second form-fitting component 42 will be explained in more detail later and is arranged as a cylinder with a flattened portion or as a non-circular component that can be moved via an opening in a side surface 212, for example via a screwdriver, a hexagonal wrench or a similar tool. By rotating about the longitudinal extension of the rotatably mounted second form-fitting component 42, it is possible to enable locking and unlocking in the joined state. The locked position or also the unlocked position can be fixed, for example, via a securing element 43 in the form of a grub screw or other locking device. The securing element 43 has an access opening formed within the end face 212, so that securing and, if necessary, actuation can be performed via the securing element 43. To this end, for example, the securing element 43 and the second form-fitting component 42 are coupled to each other via a thread or serration so that rotation of the securing element 43 can cause rotation of the second form-fitting component 42 within the second interface component 20. Reversing the direction of rotation results in a corresponding release. Securing in the respective position may be achieved, for example, by means of a self-locking thread within the bore or recess and on the outside of the securing element 43.

The groove 22 together with the tongue 12 form the sliding guide 30 between the first interface component 10 and the second interface component 20. Here, after insertion of the tongue 12 into the groove 22, all rotational degrees of freedom as well as two translational degrees of freedom are locked until the respective end stop 13, 23 is reached. After reaching the respective end stops or the end position, the electrical contacts of the plugs 29, 19 are securely contacted and the form-fitting elements 41, 42 of the locking device thus formed can be engaged with each other. The respective plug components or socket components of the electrical contacts 25 are coupled with cable connections, which in the embodiment of FIG. 1 can only be seen at the second interface component 20 in the cable connection 26. The cable connection 26 leads to further electrical or electronic components at the respective device connected to the interface assembly or interface component 20.

In addition to being configured as protruding plugs, the electrical contacts 25 may also be configured as sockets or planar elements that, in the joined position, make contact with corresponding electrical contacts of the first interface component 10. The electrical contacts 25 can be spring-mounted in order to achieve secure contacting even before reaching the end stops and a mechanical interlock via the form-fitting components 41, 42.

FIG. 2 shows the individual elements of the interface component 10, 20. The first interface component 10 with the tongue protruding beyond the base surface 11 with a dovetail profile has a plug receiver 18 which passes through the base body and the base surface 11 as well as the tongue 12. The plug 19 with the electrical contacts 15 is inserted or pushed into this plug receiver 18: in the illustrated embodiment example this is done from the underside facing away from the base surface 11. The indent on the plug 19 ensures that the upper edge of the plug 19 does not protrude beyond the upper edge of the end stop 13, and that secure locking and fixing to the first interface component 10 can take place. The rear side of the plug 19, i.e. the side facing away from the electrical contacts 15, is in full contact with the end stop 13. In the illustrated embodiment example, the rear side of the plug 15 is rounded, but other shapes may also be possible. The plug receiver 18 serves to fix the plug 19 or the plug component 19 with the electrical contacts 15 and allows the mechanical contacting forces to be absorbed and provides an abutment.

As previously explained with reference to FIG. 1, the second interface component 20 has, in addition to the continuous groove 22 starting from the end face 211, two bores 24 on the underside or base surface 21, one for receiving the second form-fitting element 42 and the other for receiving the securing element 43. Both bores 24 intersect so that the second form-fitting component 42 can make contact with the securing element 43. A circumferential groove 423 is formed at one end of the second form-fitting component 42, the groove having a bore or recess 422. A plurality of circumferentially distributed holes or recesses 422 may be formed in the circumference of the groove 423. At the end of the securing element 43 facing the second form-fitting component, for example, a spring-loaded ball or other engagement element is mounted which is preloaded towards the second form-fitting component 42 and engages the respective bores or recesses 422 when the second form-fitting component 42 is correspondingly oriented. This secures the second form-fitting component against rotation within the bore 24. Alternatively, a serration 432 may be formed on the end of the securing element 43 to engage a corresponding serration 422 within the groove 423.

The second plug component 29 with the electrical contacts 25 is inserted into a recess or receiver 28 within the second interface component 20. The plug receiver 28 allows the plug 29 and the cable guide with the cable connection 26 to be secured within the second interface component 20 in a form-fitting manner.

In FIG. 3 depicts a bottom view of the representation according to FIG. 2, from which it can be seen that the plug bushing 18 for the plug 19 is formed continuously through the first interface component 10. The corresponding cable connection 16 is shown at the bottom of the plug 19 for the first interface component 10. Both the housing and the protruding electrical contacts 25 can be seen on the plug 29 for the second interface component 20. On the upper side of the groove 22, the recesses for the plug receiver 28 can be seen, as well as the transversely extending bore 24, which in the illustrated embodiment extends over the entire width, i.e. perpendicular to a side surface 212 and perpendicular to the longitudinal extension of the groove 22. The bore diameter projects into the groove 22, so that if a cylindrical body were to be inserted into the bore 24, the tongue 12 could not be inserted completely to the end of the groove 22 or to the contact of the two end stops. To allow this to happen, a flattening 421 is formed on the second form-fitting component 42 and is sized to be flush with the top of the groove 22 or the bottom of the groove, but at least sufficiently recessed to allow the top of the tongue 121 to move along underneath.

When the tongue 12 is fully inserted into the groove 22, the recess or first form-fitting component 41 on the top surface of the tongue 12 is directly below the bore 24 and below the second form-fitting component 42. The second form-fitting component 42 can be twisted so that the rounded cylindrical portion of the surface of the second form-fitting component 42 can engage in the corresponding groove 41. Preferably, the second form-fitting component 42 fills the first form-fitting component 41 in the final state or fully joined state of the two interface components. If the tongue 12 is not yet fully inserted in the groove 22 at the beginning of the rotational movement of the second form-fitting component, the rotational movement makes up for this and moves the two interface components 10, 20 into the desired and predetermined end position. The assumed position is then fixed by engaging a preloaded ball or an engagement element or by a corresponding rotation of the securing element 43, so that the third translational degree of freedom is also locked.

FIG. 4 shows the individual components in an oblique perspective view, with the elements of the interface components 10 and 20 already joined. The plug 29 with electrical contacts 25 is inserted within the second interface component 20 within the receiver 28. The second form-fitting component 42 is located within the corresponding bore 24, the securing element 43 is engaged with the second form-fitting component 42, wherein the cylindrical portion of the second form-fitting component 42 is turned upwards so that the flattening 421, which is not shown, is advantageously flush with the top or bottom of the groove 22.

The bottom view of FIG. 4 is shown in FIG. 5, with the individual elements of the second interface component 20 only partially shown. The flattened bottom surface 421, which is flush with the top or bottom of the groove 221, can be seen, as can the arrangement of the plug 29 in the plug receiver 28. The securing element 43 engages a corresponding thread 423 via a thread 432, or a corresponding recess via a preloaded ball. Alternatively, by screwing in the securing element in the form of a grub screw, a clamping and secure fixing of the second form-fitting component 42 in the respective desired position can be achieved. The plug 19 closes flush with the underside of the base surface 11 of the first interface component 10 and the cable connection 16 projects downwardly through the interface component 10.

In FIG. 6, the final position is shown when the two interface components 10, 20 are joined. For clarity, the second interface component 20 is shown in broken lines. It can be seen that in the final joined state the two plugs 19, 29 are in contact with each other with their end faces, thus the end stops of the sliding guide consisting of groove 22 and tongue 12 have been reached. From the electrical contacts of the plug elements 19, 29, the cable connection 26 leads upwards away from the base surface 11. On the other side, the cable connection 16 is guided through the plug 19 in the opposite direction. The form-fitting element 42 is in form-fitting engagement with the groove in the tongue 12, and the securing element 43 locks the second form-fitting component in place, with accessibility from the end face 211 into the bore 24. When the second form-fitting component 42 is moved by the securing element 43, actuation and securing can occur from the end face 211, so that assembly and joining movement can occur in an orientation such that accessibility can only occur from the end face, that is, in the direction of displacement of the groove 22 and tongue 12. In principle, however, accessibility via a side surface 212 is also possible and provided.

A variant of the invention is shown in FIGS. 7 to 13. Identical reference signs denote identical components. The basic structure of the interface components 10, 20 is unchanged, so that only deviations or special features will be discussed. FIG. 7 depicts the joined position of the two interface components 10, 20. The underside or base surface of the second interface component 20 rests on the base surface 11 of the first interface component 10. The tongue 12, which projects upwardly from the base surface 11, is fully inserted into the groove in the second interface component 20. The rear side of the tongue 12 terminates with the front side 211 of the second interface component 20. A cable duct 27 is formed on the top surface of the second interface component 20, centered above the end stop 13 of the tongue 12. To the right and left of the tongue 12, holes or recesses are formed within the base body of the second interface component 20 to facilitate insertion of the tongue 12 into the groove 22.

Unlike in the first embodiment, in FIG. 7 the securing element 43 is not accessible from the front face 211 but is arranged on a side face 212. A projection is arranged or formed on the second form-fitting component 42 to prevent counterclockwise rotation from the present position. The protrusion abuts a stop formed on the second interface component 20. The securing element 43 abuts the protrusion on the side opposite the stop, thereby securing the second form-fitting component 42 against clockwise rotation. The securing element 43 may be spring-loaded such that it is preloaded towards the second interface component 20 to ensure permanent securing. To establish the form fit of the two interface components 10, 20 to each other, the securing element 43 must then be moved against a spring force from the locking position shown to an unlocking position and the second form-fitting component 42 must then be rotated clockwise to achieve the form fit previously described above. Once the protrusion rests against a stop at the bottom, complete locking is achieved and the securing element 43 can be reinserted into the recess. To release the connection, a reverse movement is performed. Only then is it possible to slide the interface component 20 away from the end stops along the sliding guide away from the first interface component 10 and release the form fit. When the two interface components are released, the electrical contacting is also released at the same time.

The released, no longer joined state of the two interface components 10, 20 is shown in FIG. 8. The two plug components 19, 20 can be seen as well as the electrical contacts 25 on the second interface component 20 and a circumferential seal 291 arranged around the electrical contacts 25. When the interface assembly is in the joined state shown in FIG. 7, the seal 291 is in contact with an end face of the corresponding plug or plug element 19 and provides a seal so that dirt and moisture cannot reach the electrical contacts.

In FIG. 9, the individual components are shown in an exploded view. The structure of the first interface component 10 corresponds to that of the embodiment according to FIGS. 1 to 6. A seal 191 is also arranged on the plug component 19, and the seals 291, 191 can abut one another or form a double seal in which one seal surrounds the other seal on the outside. This improves the sealing effect.

The cable duct 27 can be seen on the second interface component 20 as a recess on the upper side. The continuous groove 22 in a dovetail shape is also visible, as well as the transverse bores arranged in the base body of the second interface component 20. The second form-fitting component 42 has the flattening 421 on the underside, and the protrusion 425 can be seen at one end, which in the illustrated embodiment is oriented to allow the two interface components 10, 20 to be unlocked and displaced relative to each other in the illustrated position. When the second form-fitting component 42 is rotated 180°, the protrusion 425 rests at the bottom against a corresponding stop on the second interface component 20 and is secured via the securing element 43. Thus, a secured position is either in the unlocked position or in the locked position. An intermediate position is not possible due to the shape of the securing element 43. The protrusion 425 on the second form-fitting component 42 prevents the securing element 43 from being moved fully back into the locked position if there is a rotation of less than 180° from the initial position shown. The leading edge of the securing element 43 is formed with a rounding or shape that corresponds to the outer contour outside the projection 425 of the second form-fitting component 42, in the present case in the shape of a circular arc.

The securing element 43 is held or preloaded in the locked position via a spring 45, and the securing element 43 is pivotally mounted on the second interface component 20 via an axle pin 431. A securing pin 424 engages in the groove 423 in the end of the second form-fitting component 42 opposite the projection 425, so that unintentional movement in the longitudinal extension is not possible or the second form-fitting component 42 cannot fall out of the second interface component 20.

FIG. 10 shows a bottom view of the configuration shown in FIG. 9. The flattening 421 can be seen as well as the course of the bore 24 in the area of the groove 22. The plug receiver 28 for the plug 29 can be seen on the opposite side, i.e. coming from the front side.

FIG. 11 shows a bottom view of the respective interface components 10, 20 which have been completely assembled but not yet joined. The flattening 421 is parallel or flush with the top or bottom 221 of the groove 22 and substantially parallel to the base 21. The pin 424 locks the second form-fitting component 42 against falling out, and the securing element 43 rests against the projection 425 in the open position shown and prevents unintentional rotation so that smooth and complete displacement of the two interface components can occur along the sliding guide through the groove 22 and tongue 12. FIG. 11 shows the circumferential seal 229 around the electrical contacts 25.

FIG. 12 shows another representation of the state shown in FIG. 11, the plug 19 in the first interface component 10 is inserted within the end stop 13, and the electrical contacts 15 are surrounded by a seal 191. The first form-fitting component 41 in the form of the groove or cylindrical or oval recess extends transversely to the longitudinal extension of the tongue 12 and essentially parallel to the plane of the base 11. The sliding guide 30 comprising the groove 22 and the tongue 12 allows the two interface components 10, 20 to be connected by inserting the tongue 12 into the dovetail groove 22.

In the partial perspective view with the broken lines, the joined state shown in FIG. 7 can be seen in FIG. 13. The bolt 431 ensures a rotatable mounting of the securing element 43 in the second interface component 20. The second bolt 424 secures the second form-fitting component 42 against translational movement. In the position shown, form-fitting of the interface assembly has not yet occurred; for this purpose, the second form-fitting component 42 must be rotated 180° after the securing element 43 has been disengaged.

FIG. 14 shows an example of use of the interface assembly on a prosthetic hand. The prosthetic hand with the prosthetic fingers and a drive is arranged on the second interface component 20, and the groove 22 is incorporated at the proximal end. The corresponding electrical contacts 25 are arranged on the plug, which can no longer be seen, in the groove 22. The first interface component 10 is arranged as a distal end piece on a rotary adapter and is arranged on a prosthesis shaft or a forearm tube. Electrical contacting and conduction of power and data takes place via electrical contacts 25 and 15 formed or arranged on the end stop of the tongue 12.

Further examples of use are shown in FIG. 15, in which the interface assembly is formed once between a thigh shaft and a prosthetic knee joint and a lower leg tube and a prosthetic foot.

In addition to secure, form-fitting attachment of the respective components to one another, the interface assembly also provides electrical contacting and shielding of the electrical contacting against contamination and moisture. A buckling-resistant, secure contacting with a simultaneous mechanical locking is provided.

The invention claimed is:

1. An interface assembly with a first interface component (10) and a second interface component (20) with a sliding guide (30) for mechanically fixing the interface components (10, 20) to one another, wherein a tongue (12) projecting from a base surface (11) is arranged on one of the interface components (10) and a groove (22) with corresponding cross sections located in a base surface (21) is arranged on the other interface component (20), wherein the tongue (12) and the groove (22) lock the interface components (10, 20) to each other in a form-fitting manner and block a movement perpendicular to the base surfaces and perpendicular to the longitudinal extension of the tongue (12) and groove (22), wherein electrical contact elements (15, 25) are arranged on the tongue (12) and in the groove (22), said contact elements establishing an electrical connection in a joined state of the interface components (10, 20), and wherein the groove (22) is sealed on the end face in the joined state with the tongue (12).

2. The interface assembly according to claim 1, wherein the electrical contact elements (15, 25) are arranged on an end face of an end stop (13) of the tongue (12) and/or on an end face of an end stop (23) of the groove (22).

3. The interface assembly according to claim 2, wherein the end stop (13, 23) forms a contact surface for a plug (19, 29) or a socket with the contact elements (15, 25).

4. The interface assembly according to claim 1, wherein a cable connection (16, 26) is laid by the electrical contact elements (15, 25) leading away from the tongue (12) and the groove (22).

5. The interface assembly according to claim 1, wherein a cable duct (27) and/or a plug receiver (18, 28) is arranged or formed in at least one interface component (10, 20).

6. The interface assembly according to claim 1, wherein the interface components (10, 20) have a locking device (41,

42) which blocks displacement of interface components (10, 20) relative to one another along the longitudinal extent of the sliding guide (30).

7. The interface assembly according to claim 6, wherein the locking device comprises two form-fitting components (41, 42) which can be repeatedly engaged and disengaged with each other.

8. The interface assembly according to claim 7, wherein one form-fitting component (42) is rotatably or pivotally mounted and has at least one flattening (421), non-circular cross-section or recess.

9. The interface assembly according to claim 7, wherein at least one form-fitting component (42) braces the interface components (10, 20) against each other in the locked position.

10. The interface assembly according to claim 6, wherein at least one form-fitting component (42) is assigned a securing element (43) which is accessible from an end face (211) of the interface component (20).

11. The interface assembly according to claim 10, wherein the securing element (43) engages in the form-fitting component (42) in a form-fitting manner, is preloaded against the form-fitting component (42) and/or is coupled to the form-fitting component (42) via a toothing (432).

12. The interface assembly according to claim 7, wherein at least one form-fitting component (41) is designed as a groove.

13. The interface assembly according to claim 1, wherein the first interface component (10) is designed as a distal end plate of a prosthesis socket or a prosthesis component.

14. The interface assembly according to claim 1, wherein the second interface component (20) is formed as a proximal end component of a prosthetic hand or a prosthetic gripping device.

* * * * *